United States Patent
Bonar Fernando et al.

(10) Patent No.: US 9,662,074 B2
(45) Date of Patent: May 30, 2017

(54) BIOLOGICAL INFORMATION MONITORING SYSTEM, DEVICE, METHOD, AND PROGRAM

(71) Applicant: Panasonic Intellectual Property Management Co., Ltd., Osaka (JP)

(72) Inventors: Jeffry Bonar Fernando, Osaka (JP); Jun Ozawa, Nara (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 14/738,981

(22) Filed: Jun. 15, 2015

(65) Prior Publication Data
US 2015/0366515 A1   Dec. 24, 2015

(30) Foreign Application Priority Data
Jun. 24, 2014   (JP) .................. 2014-128900

(51) Int. Cl.
*A61B 5/04*   (2006.01)
*A61B 5/00*   (2006.01)
(Continued)

(52) U.S. Cl.
CPC .......... *A61B 5/7278* (2013.01); *A61B 5/0452* (2013.01); *A61B 5/0809* (2013.01); *A61B 5/0816* (2013.01)

(58) Field of Classification Search
CPC ... A61B 5/0452; A61B 5/0468; A61B 5/0472; A61B 5/0006; A61B 5/0402;
(Continued)

(56) References Cited

U.S. PATENT DOCUMENTS

2005/0197586 A1* 9/2005 Pearlman ........... A61B 5/04525
                                                        600/509
2006/0041201 A1* 2/2006 Behbehani ........... A61B 5/0456
                                                        600/521
(Continued)

OTHER PUBLICATIONS

Jeffry Bonar Fernando et al., "Estimation of respiratory signal from thoracic impedance cardiography in low electrical current", International Conference of the IEEE Engineering in Medicine and Biology Society, p. 3829-3832(2013).

*Primary Examiner* — Edward Moran
*Assistant Examiner* — Natasha Patel
(74) *Attorney, Agent, or Firm* — Wenderoth, Lind & Ponack, L.L.P.

(57) ABSTRACT

A biological information monitoring system includes: a measuring circuitry configured acquire information on a potential difference between two first electrodes that is placed on a first thorax of a user, wherein the first thorax is in a symmetric position to a second thorax that is positioned at the same side as a heart of the user; a detection circuitry configured to detect a plurality of S wave peaks based on the information on the potential difference to generate time-series information on the plurality of S wave peaks; and a processing circuitry configured to determine respiratory information on the user based on the time-series information on the plurality of S wave peaks, and to output the respiratory information as biological information.

7 Claims, 17 Drawing Sheets

(51) Int. Cl.
 *A61B 5/0452* (2006.01)
 *A61B 5/08* (2006.01)
(58) Field of Classification Search
 CPC ... A61B 5/7282; A61B 5/0205; A61B 5/0816;
 A61N 1/36592
 See application file for complete search history.

(56) References Cited

U.S. PATENT DOCUMENTS

2011/0245698 A1* 10/2011 Wang ................ A61B 5/024
 600/509
2012/0190994 A1* 7/2012 Kim ................ A61B 5/0402
 600/509

* cited by examiner

BIOLOGICAL INFORMATION MONITORING SYSTEM, DEVICE, METHOD, AND PROGRAM

BACKGROUND

1. Field of the Invention

The present application relates to a technique for extracting respiration. More particularly, the present application relates to a technique for measuring impedance of a living body by using a plurality of electrodes placed on a body of a user, and for extracting information regarding respiration.

2. Description of the Related Art

In recent years, methods for measuring and recording body conditions of a user electrically and mechanically over an extended period of time are coming into widespread adoption. Examples of basic electrical information that represents body conditions of a user include an electroencephalogram (EEG) related to a brain and an electrocardiogram (ECG) related to motion of a heart. Among these information items, the electrocardiogram is acquired, for example, as fundamental biological information (vital sign) at a hospital. In addition, the electrocardiogram can also be acquired by using a portable electrocardiograph called a Holter electrocardiograph, if there is suspicion of a cardiac disease. Use of the Holter electrocardiograph enables recording of an electrocardiogram over a long period of time, for example, 24 hours, at a place other than a hospital, such as at home. In recent years, this Holter electrocardiograph has been downsized, and a user can measure the electrocardiogram more simply.

Recording the electrocardiogram over a long period of time by using the Holter electrocardiograph allows detection of symptoms that cannot be detected during a short examination at a hospital, such as arrhythmia. However, there are examination items (cases) that can be detected by a prolonged examination besides the electrocardiogram. Examples of such a case include sleep apnea syndrome. Sleep apnea syndrome is a respiratory disease closely related to arrhythmia.

Estimation of sleep apnea syndrome cannot be performed only with the electrocardiogram, but information regarding respiration is also required. Estimation of sleep apnea syndrome requires an all-night sleep polygraph examination for measuring the electrocardiogram, respiration, and electroencephalogram simultaneously. This examination needs to be performed by a patient staying at a hospital, and is burdensome to both the patient and the hospital. For this reason, in a stage of suspected disease, it is not realistic to perform such burdensome examinations.

If information regarding a respiratory disease, specifically, information regarding a respiratory rate can be acquired as simply as acquiring the electrocardiogram by using the Holter electrocardiograph, earlier detection of a disease and acceleration of diagnosis are likely to be achieved.

So far, a medical device called a pulse oximeter has mainly been used for simple respiratory measurement. This is a measuring instrument for examining arterial oxygen saturation. Arterial oxygen saturation is measured by wearing a sensor, which is called a probe, on a fingertip. This measuring instrument has a red light source or an LED that emits red light, and measures oxygen content contained in an artery inside a finger in real time by measuring transmitted light of the finger with the sensor. In this way, when both the electrocardiogram and respiratory information are required, it is necessary to place electrodes for the electrocardiograph on a thorax, and to wear the probe of the pulse oximeter on a fingertip.

So far, simultaneous acquisition of the electrocardiogram and the respiratory information with one device, and separation of the respiratory information from data acquired by using the electrocardiogram information have been addressed. One approach is an impedance method. According to the impedance method, an electric current is passed through a body of a user, and the electrocardiogram and impedance change due to respiration are measured with electrodes placed on a thorax. For example, NPL 1 describes a method for extracting respiratory information from thoracic impedance in low electric current (10 nA).

Before description of a concept of the method described in NPL 1, basic electrocardiographic components will be described. FIG. 1 illustrates one cycle of basic electrocardiographic components. The electrocardiogram includes peaks called a P wave, a Q wave, an R wave, an S wave, and a T wave. A portion of the QRS waves represents ventricular activation.

FIG. 2A to FIG. 2C illustrate a concept of the method described in NPL 1. In measurement, four electrodes are placed on a center of a thorax (see FIG. 2A). In FIG. 2A, potential is measured with two inner electrodes among the four aligned electrodes, excluding a ground electrode. A low electric current (10 nA) is passed between two outer electrodes. FIG. 2B illustrates thoracic impedance measured from the potential. NPL 1 defines an envelope curve of the T wave of components derived from the electrocardiogram as respiratory information.

In NPL 1, the four electrodes are attached to the center of the thorax to measure thoracic impedance. In an experiment of NPL 1, a subject is asked to breathe four phases of respiration: normal breath, deep breath, stop breathing, and normal breath. The subject was instructed to take a breath 15 times with a three-second cycle during the normal breath phase. The subject was instructed to take a breath eight times with a five-second cycle during the deep breath phase. The subject was instructed to stop breathing for 30 seconds during the stop-breathing phase.

FIG. 2C illustrates an extraction result of respiration. The cycle in the envelope curve has correlation with an actual breath. In addition, amplitude while breathing is stopped is extremely small, and amplitude during the deep breath is also larger than amplitude during the normal breath, and thus extracted respiratory information represents actual breath.

CITATION LIST

Non-Patent Literature

NPL 1: Jeffry Bonar Fernando, et.al. "Estimation of respiratory signal from thoracic impedance cardiography in low electrical current", International Conference of the IEEE Engineering in Medicine and Biology Society, pp. 3829-3832 (2013)

The above-mentioned conventional technique requires improvement in the technique for extracting respiration more correctly.

SUMMARY OF THE INVENTION

One non-limiting and exemplary embodiment according to the present application provides a system, a device, a method, and a program for monitoring respiratory information which is biological information by using electrocardiography.

In order to solve the above problems, a biological information monitoring system according to one aspect of the present disclosure includes: a measuring circuitry configured acquire information on a potential difference between two first electrodes that is placed on a first thorax of a user, wherein the first thorax is in a symmetric position to a second thorax that is positioned at the same side as a heart of the user; a detection circuitry configured to detect a plurality of S wave peaks based on the information on the potential difference to generate time-series information on the plurality of S wave peaks; and a processing circuitry configured to determine respiratory information on the user based on the time-series information on the plurality of S wave peaks, and to output the respiratory information as biological information.

The aforementioned general and specific aspect may be implemented as a device, a method, and a computer program, besides the system, or any selective combination of a system, a device, a method.

The biological information monitoring system, device, method, and computer program according to one aspect of the present disclosure allow extraction of the respiratory information of the user, even if the user places the electrodes on the thorax on the opposite side of the position of the heart.

DETAILED DESCRIPTION

The present inventors have found out that a technique of NPL 1 described above can acquire respiratory information more accurately under predetermined conditions.

That is, the present inventors have found out that, when an electrode group is placed on a thorax, accuracy of respiratory information may vary depending on a position of the electrode group. Specifically, the present inventors have found out that, when the electrode group is placed on the thorax on an opposite side of a position of a heart, respiration may not be extracted correctly. Most people have a heart in the left thorax. Accordingly, "opposite side of the position of the heart" typically means the right thorax.

Figure 3A:
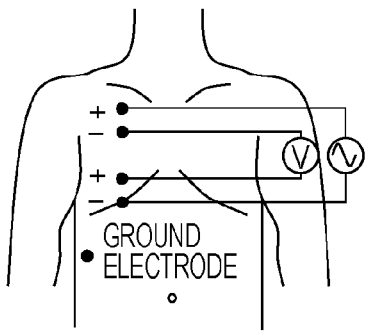
FIG. 3A is a diagram illustrating how an electrode group is placed on a right thorax of a user.

FIG. 3A is a diagram illustrating the electrode group placed on the right thorax. It is assumed that the heart of a subject is on the left side of the thorax.

Figure 3B:
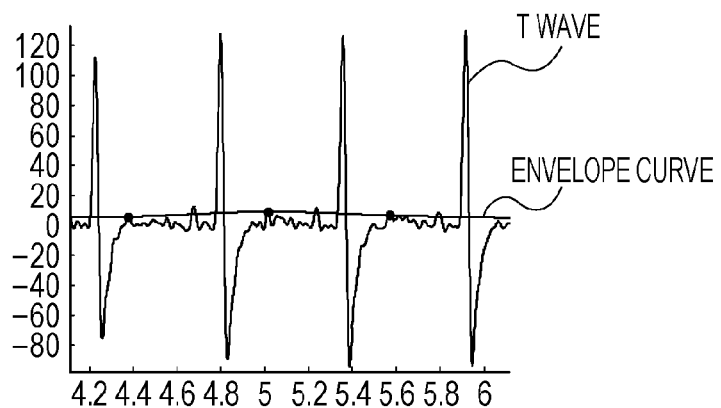
FIG. 3B is a diagram illustrating a waveform of measured thoracic impedance and an envelope curve of a T wave.

FIG. 3B illustrates a waveform of measured thoracic impedance. The subject is instructed to repeat a breath with a four-second cycle for 32 seconds during measurement. FIG. 3B also illustrates an envelope curve of a T wave.

Figure 3C:
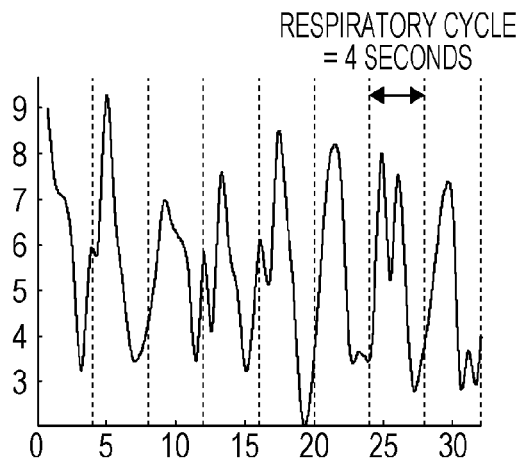
FIG. 3C is a diagram illustrating respiratory information clearly illustrated by changing a scale of the envelope curve of the T wave peaks.

FIG. 3C illustrates a result of extraction of respiratory information from the envelope curve of T wave peaks obtained from the measured thoracic impedance. A period between dashed lines represents one cycle of respiration. If the respiratory information is extracted correctly, one peak is supposed to be observed. However, two or more peaks are observed in many respiratory cycles.

The present inventors have examined a reason. One possible reason is that amplitude of the T wave has become very small. This is attributed to an electrocardiography-derived component in impedance having become smaller than the component measured when the electrodes are placed on a center of the thorax, because the electrodes are placed distant from the heart. That is, the amplitude of the T wave becomes closer to a noise level of a sensor, and thus a peak value is likely to be buried in the noise.

Next, the present inventors have examined a possibility that the electrode group is placed on the thorax on the opposite side of the position of the heart (hereinafter referred to as right thorax for convenience) of a user. For example, the user is highly likely to place the electrode group on the right thorax by mistake at home. In addition, it is highly likely that the electrode group cannot be placed at a specified position due to inconvenience such as a wound made by a surgical operation or the like. In conclusion, there is a strong possibility that the electrode group will be placed on the right thorax of the user. Particularly in a latter case, it is necessary to place the electrode group on the right thorax intentionally.

The following describes an experiment performed by the present inventors and findings obtained for extracting the respiratory information more correctly when the electrode group is placed on the thorax on the opposite side of the position of the heart (right thorax) of the user.

(Findings from Experiment)

Figure 4A:
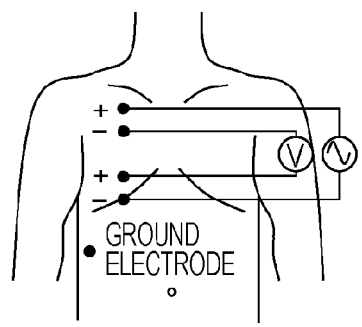
FIG. 4A is a diagram illustrating the electrode group placed on the right thorax of the user.
Figure 4B:
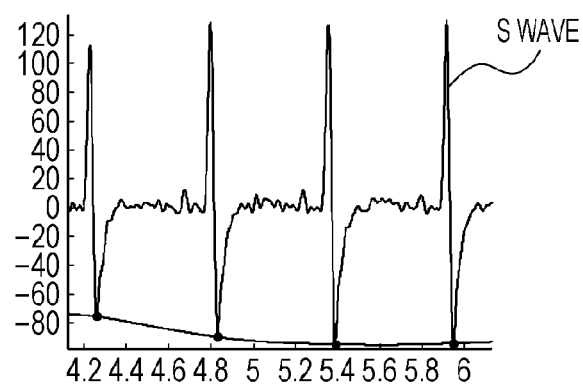
FIG. 4B is a diagram illustrating a waveform of impedance measured by using the electrodes placed on the right side of the thorax and an envelope curve of an S wave.

FIG. 4A illustrates the electrode group placed on the right thorax of the user. FIG. 4B illustrates a waveform of impedance measured by using the electrodes placed on the right side of the thorax. This waveform is identical to the thoracic impedance waveform measured in FIG. 3. FIG. 4B also illustrates an envelope curve of an S wave.

Figure 4C:
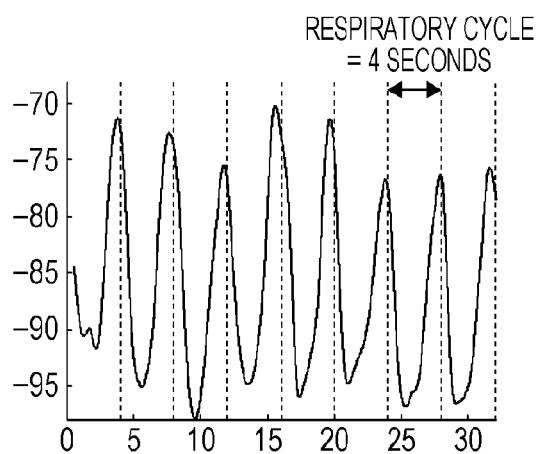
FIG. 4C is a diagram illustrating respiratory information clearly illustrated by changing a scale of the envelope curve of the S wave peaks.

FIG. 4C illustrates a result of extraction of the respiratory information from the envelope curve of S wave peaks obtained from the measured thoracic impedance. Since only one peak exists in every cycle, it is understood that FIG. 4C represents actual respiration accurately.

Next, the present inventors have examined how accurately the envelope curve of peaks of the P wave, Q wave, R wave, S wave, and T wave represents actual respiration depending on electrode positions. The subject is instructed to take a breath with a four-second cycle for 32 seconds while changing the electrode position to three points (center, right side, and left side of the thorax). It is assumed that the heart of the subject is on the left side of the thorax.

Figure 5A:
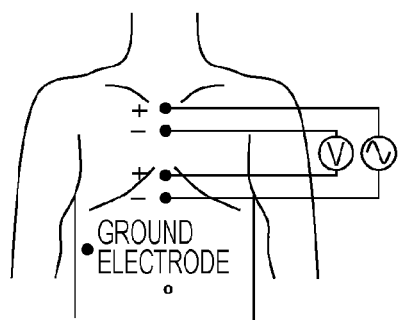
FIG. 5A is a diagram illustrating an example of placement of the electrode group on a center of the thorax.
Figure 6A:
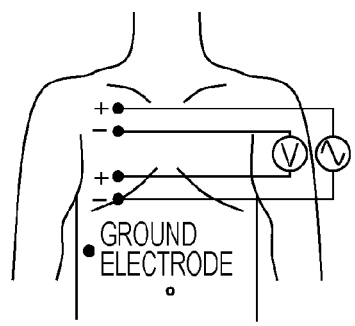
FIG. 6A is a diagram illustrating an example of placement of the electrode group on the right thorax.
Figure 7A:
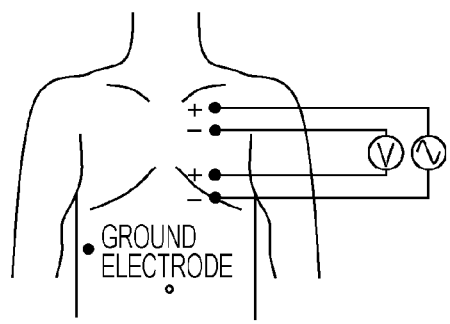
FIG. 7A is a diagram illustrating an example of placement of the electrode group on a left thorax.

FIG. 5A, FIG. 6A, and FIG. 7A illustrate examples of placement of the electrode group placed on the center of the thorax, on the right thorax, and on the left thorax, respectively.

Figure 5B:
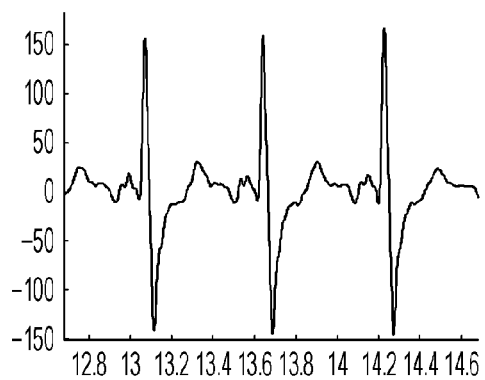
FIG. 5B is a diagram illustrating a waveform of thoracic impedance, and is a diagram illustrating an envelope curve of a P wave, Q wave, R wave, S wave, and T wave.
Figure 5C:
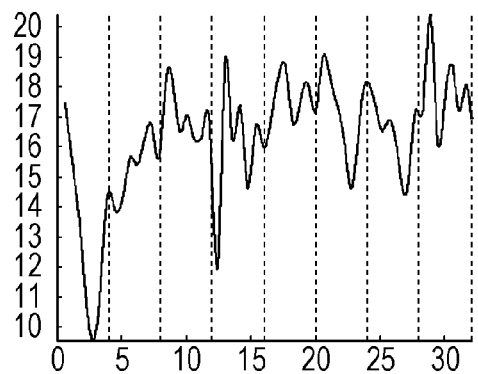
FIG. 5C is a diagram illustrating a waveform of thoracic impedance, and is a diagram illustrating an envelope curve of the P wave, Q wave, R wave, S wave, and T wave.
Figure 5D:
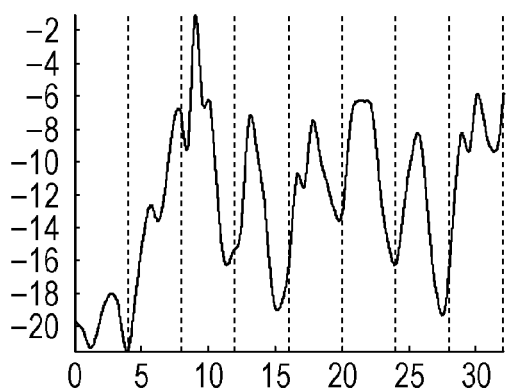
FIG. 5D is a diagram illustrating a waveform of thoracic impedance, and is a diagram illustrating an envelope curve of the P wave, Q wave, R wave, S wave, and T wave.
Figure 5E:
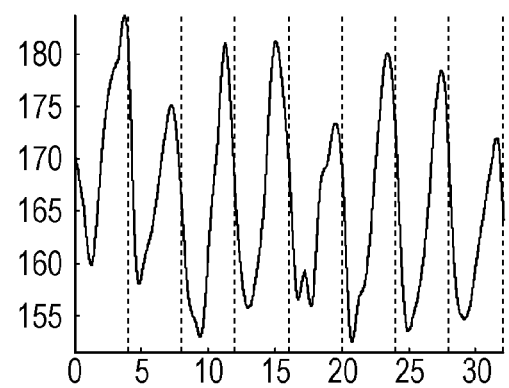
FIG. 5E is a diagram illustrating a waveform of thoracic impedance, and is a diagram illustrating an envelope curve of the P wave, Q wave, R wave, S wave, and T wave.
Figure 5F:
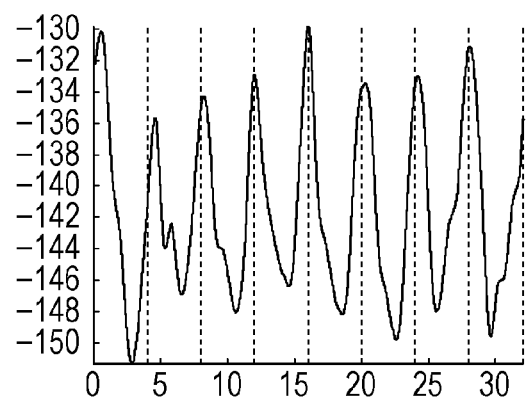
FIG. 5F is a diagram illustrating a waveform of thoracic impedance, and is a diagram illustrating an envelope curve of the P wave, Q wave, R wave, S wave, and T wave.
Figure 5G:
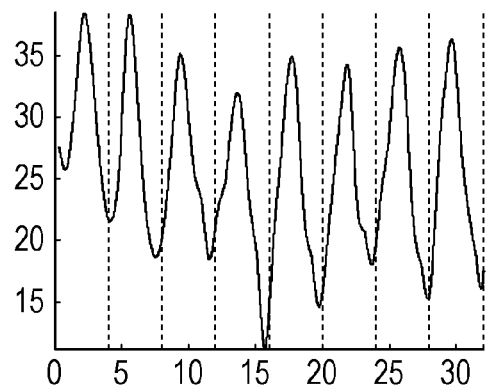
FIG. 5G is a diagram illustrating a waveform of thoracic impedance, and is a diagram illustrating an envelope curve of the P wave, Q wave, R wave, S wave, and T wave.

FIG. 5B illustrates a waveform of thoracic impedance measured by using the electrodes placed on the center of the thorax. FIG. 5C to FIG. 5G illustrate the envelope curves of the P wave, Q wave, R wave, S wave, and T wave, respectively. It is determined that the envelope curve of the T wave of FIG. 5G best represents the actual respiration. Among the P wave, Q wave, R wave, S wave, and T wave, large peak amplitude is exhibited in the R wave, S wave, and T wave. Since a width of the T wave peak is larger than a width of other two peaks, a correct peak value is likely to be sampled more stably.

Figure 6B:
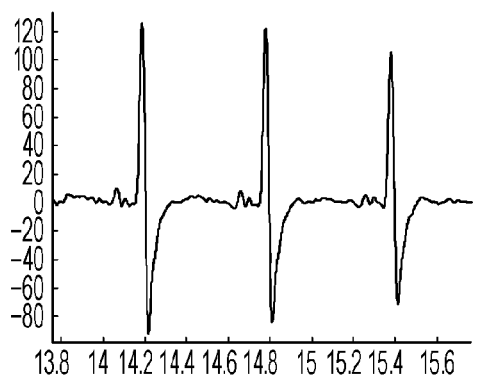
FIG. 6B is a diagram illustrating a waveform of thoracic impedance, and is a diagram illustrating an envelope curve of the P wave, Q wave, R wave, S wave, and T wave.
Figure 6C:
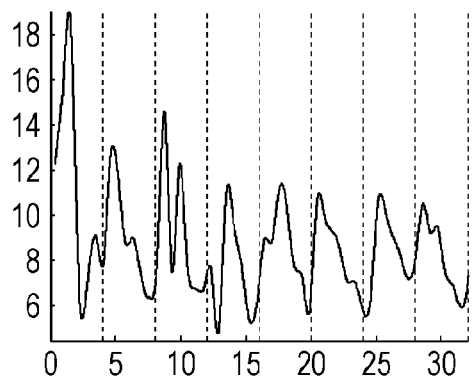
FIG. 6C is a diagram illustrating a waveform of thoracic impedance, and is a diagram illustrating an envelope curve of the P wave, Q wave, R wave, S wave, and T wave.
Figure 6D:
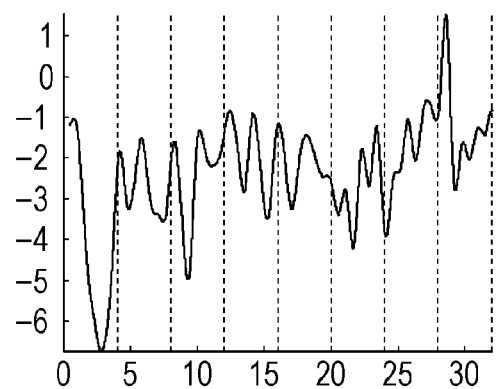
FIG. 6D is a diagram illustrating a waveform of thoracic impedance, and is a diagram illustrating an envelope curve of the P wave, Q wave, R wave, S wave, and T wave.
Figure 6E:
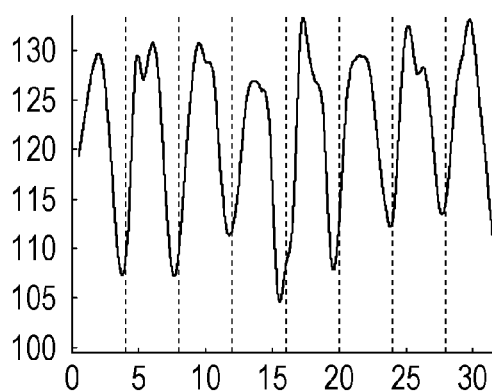
FIG. 6E is a diagram illustrating a waveform of thoracic impedance, and is a diagram illustrating an envelope curve of the P wave, Q wave, R wave, S wave, and T wave.
Figure 6F:
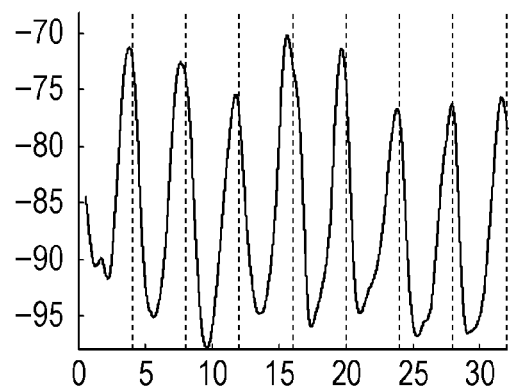
FIG. 6F is a diagram illustrating a waveform of thoracic impedance, and is a diagram illustrating an envelope curve of the P wave, Q wave, R wave, S wave, and T wave.
Figure 6G:
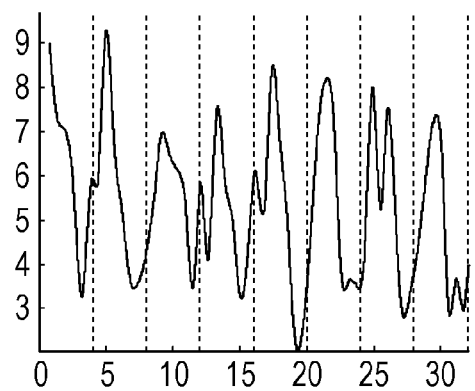
FIG. 6G is a diagram illustrating a waveform of thoracic impedance, and is a diagram illustrating an envelope curve of the P wave, Q wave, R wave, S wave, and T wave.

FIG. 6B illustrates a waveform of thoracic impedance measured by using the electrodes placed on the right side of the thorax. FIG. 6C to FIG. 6G illustrate the envelope curves of the P wave, Q wave, R wave, S wave, and T wave, respectively. It is determined that the envelope curve of the S wave of FIG. 6F best represents the actual respiration. When the electrode group is placed on the right side of the thorax, the electrocardiography-derived component in impedance becomes smaller as a whole, as compared with a case where the electrode group is placed on the center of the thorax. That is, the amplitude of the T wave also becomes very small. Since the amplitude of the T wave becomes closer to the noise level of the sensor, the peak value is easily buried in the noise. Among the P wave, Q wave, R wave, S wave, and T wave, large peak amplitude is exhibited in the R wave and S wave. Since a width of the S wave peak is larger than a width of the R wave peak, the correct peak value is likely to be sampled more stably.

Figure 7B:
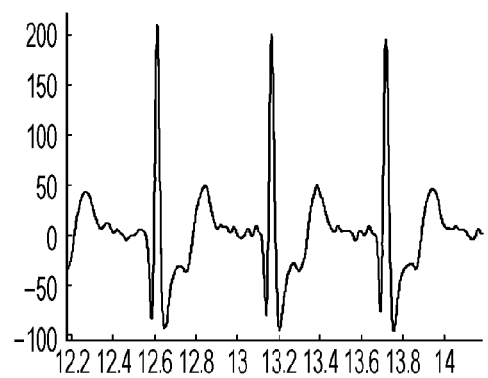
FIG. 7B is a diagram illustrating a waveform of thoracic impedance, and is a diagram illustrating an envelope curve of the P wave, Q wave, R wave, S wave, and T wave.
Figure 7C:
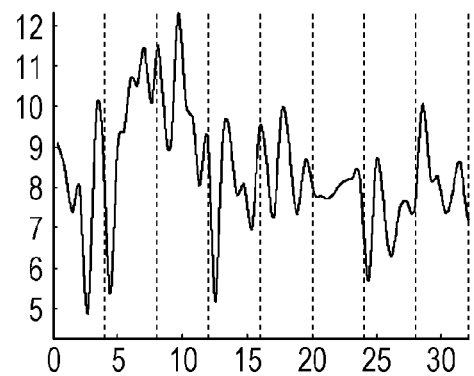
FIG. 7C is a diagram illustrating a waveform of thoracic impedance, and is a diagram illustrating an envelope curve of the P wave, Q wave, R wave, S wave, and T wave.
Figure 7D:
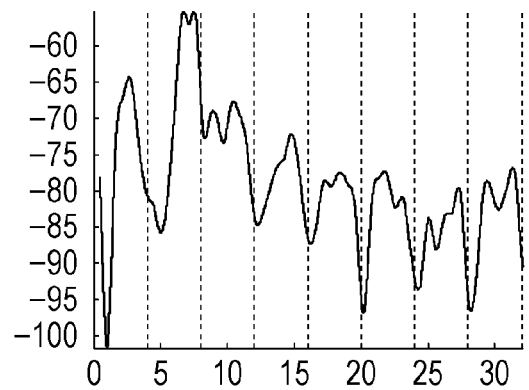
FIG. 7D is a diagram illustrating a waveform of thoracic impedance, and is a diagram illustrating an envelope curve of the P wave, Q wave, R wave, S wave, and T wave.
Figure 7E:
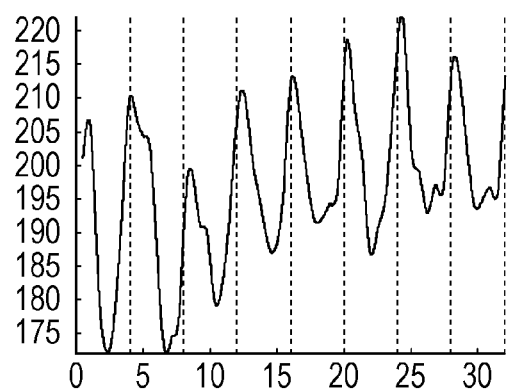
FIG. 7E is a diagram illustrating a waveform of thoracic impedance, and is a diagram illustrating an envelope curve of the P wave, Q wave, R wave, S wave, and T wave.
Figure 7F:
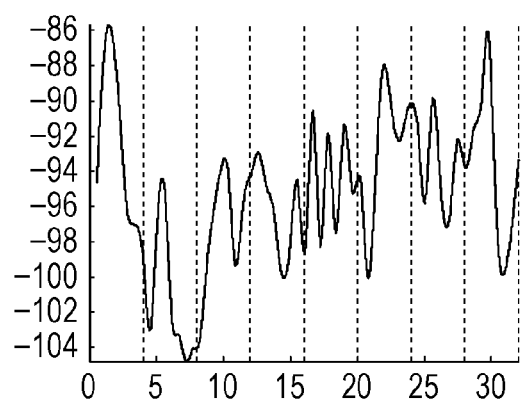
FIG. 7F is a diagram illustrating a waveform of thoracic impedance, and is a diagram illustrating an envelope curve of the P wave, Q wave, R wave, S wave, and T wave.
Figure 7G:
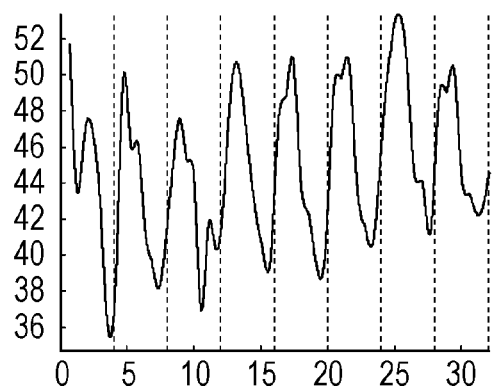
FIG. 7G is a diagram illustrating a waveform of thoracic impedance, and is a diagram illustrating an envelope curve of the P wave, Q wave, R wave, S wave, and T wave.

FIG. 7B illustrates a waveform of thoracic impedance measured by using the electrodes placed on the left side of the thorax. FIG. 7C to FIG. 7G illustrate the envelope curves of the P wave, Q wave, R wave, S wave, and T wave, respectively. It is determined that the envelope curve of the T wave of FIG. 7G best represents the actual respiration. Among the P wave, Q wave, R wave, S wave, and T wave, large peak amplitude is exhibited in the Q wave, R wave, S wave, and T wave. Since the width of the T wave peak is larger than the width of other three peaks, the correct peak value is likely to be sampled more stably.

As a result of the above-described experiment, the present inventors have obtained findings that it is determined the envelope curve of the S wave represents the actual respiration most correctly, when the electrode group is placed on the thorax on the opposite side of the position of the heart of the user.

An outline of one aspect of the present disclosure is as follows.

An outline of one aspect of the present disclosure is as follows.

A biological information monitoring system according to one aspect of the present disclosure includes a measuring circuitry for measuring a potential difference between two electrodes placed on a thorax on an opposite side of a position of a heart of a user and for acquiring information regarding the potential difference, a detection circuitry for detecting electrocardiographic S wave peaks based on information regarding the potential difference acquired by the measuring circuitry, a processing circuitry for extracting respiratory information regarding respiration of the user from time-series information on the S wave peaks detected by the detection circuitry, and an output circuitry for outputting the respiratory information extracted by the processing circuitry.

In an exemplary embodiment, the measuring circuitry includes a current source for supplying a current to the two electrodes, and an impedance-measuring circuitry for measuring a potential difference between the two electrodes when the current is applied to the two electrodes, and for measuring an impedance value from the current value and the potential difference. The measuring circuitry acquires the impedance value as information regarding the potential difference.

In an exemplary embodiment, when another two electrodes different from the above-described two electrodes are further provided on the thorax of the user, the measuring circuitry includes a current source for supplying a current between the two another electrodes, and an impedance-measuring circuitry for measuring a potential difference between the two electrodes provided between the two another electrodes when the current is applied to the another two electrodes, and for measuring an impedance value from the current value and the potential difference. The measuring circuitry acquires the impedance value as information regarding the potential difference.

A biological information monitoring device according to another aspect of the present disclosure includes a detection circuitry for receiving information regarding a potential difference from a measuring device for measuring the potential difference between two electrodes placed on a thorax on an opposite side of a position of a heart of a user, and for detecting electrocardiographic S wave peaks based on the information regarding the potential difference, a processing circuitry for extracting respiratory information regarding the respiration of the user from time-series information on the S wave peaks detected by the detection circuitry, and an output circuitry for outputting the respiratory information extracted by the processing circuitry.

In an exemplary embodiment, the detection circuitry detects, as the S wave peak, a peak that is equal to or less than a predetermined threshold in one electrocardiographic cycle based on the information regarding the potential difference acquired by the measuring device.

In an exemplary embodiment, the detection circuitry detects the R wave in one electrocardiographic cycle based on the information regarding the potential difference acquired by the measuring device, and then detects a minimum value after the R wave as the S wave peak.

In an exemplary embodiment, the detection circuitry detects the R wave and the T wave in one electrocardiographic cycle based on the information regarding the potential difference acquired by the measuring device, and detects, as the S wave peak, a peak having polarity opposite to polarity of the R wave and the T wave, the peak existing between the R wave and the T wave.

A method for monitoring biological information according to still another aspect of the present disclosure involves the steps of: (a) receiving information on a potential difference from a measuring device for measuring the potential difference between two electrodes placed on a thorax on an opposite side of a position of a heart of a user; (b) detecting electrocardiographic S wave peaks based on the information on the potential difference; (c) extracting respiratory information regarding respiration of the user from time-series information on the S wave peaks detected in the step (b); and (d) outputting the respiratory information extracted in the step (c).

In an exemplary embodiment, the method for monitoring biological information involves, in the step (b), the step of detecting, as the S wave peak, a peak equal to or less than a predetermined threshold in one electrocardiographic cycle based on the information regarding the potential difference acquired by the measuring device.

In an exemplary embodiment, the method for monitoring biological information involves, in the step (b), the steps of: detecting the R wave in one electrocardiographic cycle based on the information regarding the potential difference acquired by the measuring device; and detecting a minimum value after the R wave as the S wave peak.

In an exemplary embodiment, the method for monitoring biological information involves, in the step (b), the steps of: detecting the R wave and the T wave in one electrocardiographic cycle based on the information regarding the potential difference acquired by the measuring device; and detecting, as the S wave peak, a peak having polarity opposite to polarity of the R wave and the T wave, the peak existing between the R wave and the T wave.

A computer program executed by a computer provided in the biological information monitoring system according to another aspect of the present disclosure causes the computer to: (a) receive the information regarding the potential difference from the measuring device for measuring the potential difference between two electrodes placed on the thorax on the opposite side of the position of the heart of the user; (b) detect the electrocardiographic S wave peaks based on the information regarding the potential difference; (c) extract respiratory information regarding the respiration of the user from time-series information on the detected S wave peaks; and (d) output the extracted respiratory information.

Figure 8A:
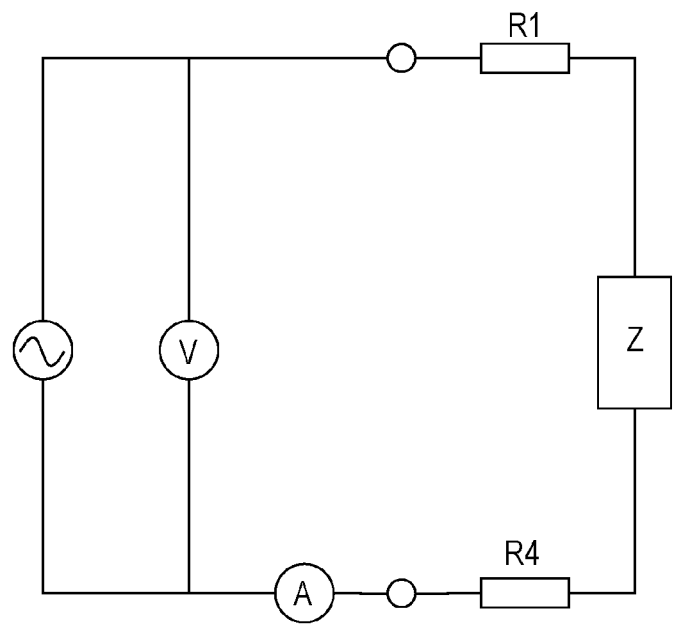
FIG. 8A is a diagram illustrating a schematic circuitry configuration of a two-terminal method.
Figure 8B:
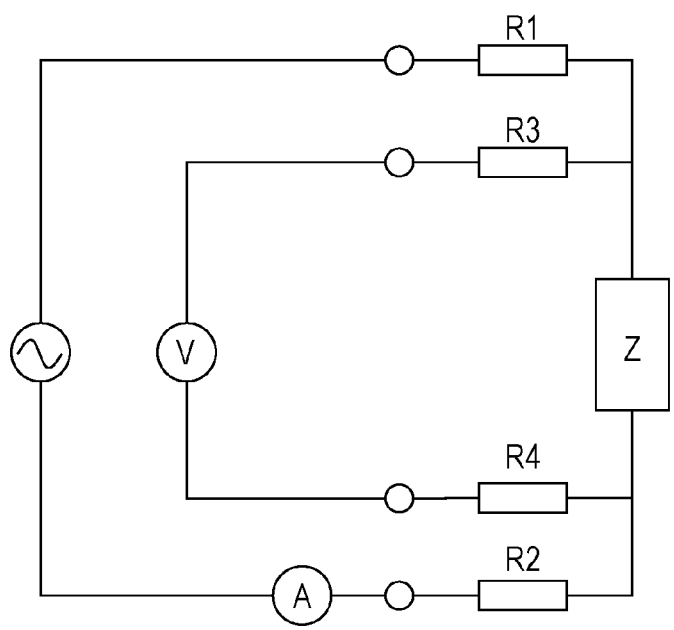
FIG. 8B is a diagram illustrating a schematic circuitry configuration of a four-terminal method.

Prior to a description of an exemplary embodiment, a configuration for measuring thoracic impedance will be described. FIG. 8A is a diagram illustrating a schematic circuitry configuration of a two-terminal method, whereas FIG. 8B is a diagram illustrating a schematic circuitry configuration of a four-terminal method. Z represents impedance of a target to be measured, and R1 to R4 each represent contact impedance between an electrode and skin. A circle on the diagrams corresponds to an electrode.

The two-terminal method of FIG. 8A is used to measure Z+R1+R2. Meanwhile, the four-terminal method of FIG. 8B is used to measure only Z. Therefore, in measurement of thoracic impedance, when an influence of the contact impedance between an electrode and skin is to be eliminated, the four-terminal method is used. That is, it can be said that impedance measured by the four-terminal method is more accurate than impedance measured by the two-terminal method.

Variations in thoracic impedance are based on activities (heartbeat) of a heart and activities (respiration) of a lung. The activities (heartbeat) of the heart vary impedance because, when the heart conducts mechanical activities including contraction and extension, cardiac muscle cells are electrically activated (depolarization) and returned (repolarization). This electric change of the cardiac muscle cells brings about variations in impedance. Meanwhile, the activities (respiration) of the lung vary impedance from the following reason. That is, during inspiration, air is taken into alveoli, which inhibits an electric current from flowing. This results in higher impedance. Meanwhile, air is discharged during expiration, which facilitates a flow of the electric current. This results in lower impedance. When the electrodes are attached to both hands to measure impedance, impedance between both hands exhibits variations produced by heartbeat and variations produced by respiration.

The following exemplary embodiment will be described assuming that the thorax on the opposite side of the position of the heart of the user is the right thorax. When the position of the heart of the user is in the right thorax, the thorax on the opposite side of the position of the heart of the user becomes the left thorax.

Note that some people have an opinion that a human heart is positioned almost in a center of a body. According to the opinion, it is assumed that "a position of a heart of a user" of the present specification denotes a position on a side of a ventricle (typically left ventricle) that pumps blood to an aorta. This is because developed muscles on the side of the ventricle cause contraction and extension of the muscles to be obtained strongly in the electrocardiogram.

The exemplary embodiment according to the present disclosure will be described below with reference to the accompanying drawings.

(Embodiment 1)

Figure 9:
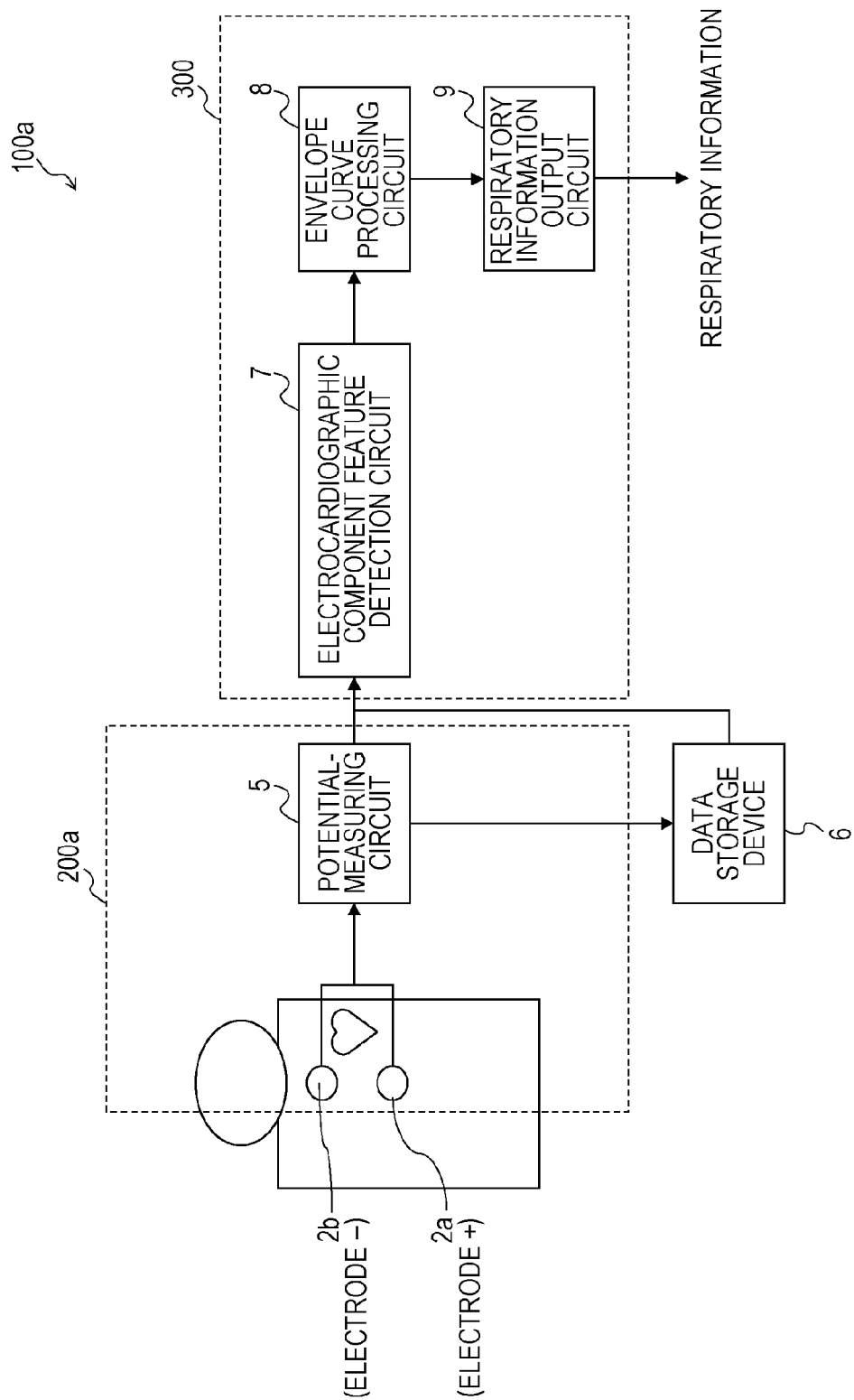
FIG. 9 is a diagram illustrating a configuration of biological information monitoring system $100a$ according to an exemplary embodiment.

FIG. 9 illustrates a configuration of biological information monitoring system 100a according to the present exemplary embodiment. Biological information monitoring system 100a measures thoracic impedance by a two-terminal method.

Biological information monitoring system 100a includes data storage device 6, biological signal measuring device 200a, and biological information monitoring device 300.

Biological signal measuring device 200a includes electrodes 2a and 2b, and potential-measuring circuitry 5. An implementation form of biological signal measuring device 200a as hardware is, for example, a potential sensor with electrodes placed on a thorax of a user.

Potential-measuring circuitry 5 uses electrodes 2a and 2b to measure a potential difference between electrodes 2a and 2b. Electrodes 2a and 2b are placed on the thorax on an opposite side of a position of a heart of the user. For example, the thorax of the user is divided into a first area and a second area by a central line of the thorax. The first thorax is in a symmetric position to a second thorax that is positioned at the same side as a heart of the user. When the heart is positioned in the first area, electrodes 2a and 2b are placed in the second area on the opposite side of the first area.

In the present exemplary embodiment, it is assumed that electrodes 2a and 2b are placed on the right thorax of the user. A ground electrode (not illustrated) may be provided, a potential difference between electrode 2a and the ground and a potential difference between electrode 2b and the ground may be determined, and a difference between these two potential differences may be determined as the potential difference.

Potential-measuring circuitry 5 may apply an electric current and measure impedance while measuring potential with electrode 2a and electrode 2b. An impedance value is obtained by division of the potential difference measured with electrode 2a and electrode 2b by the applied current value.

Potential-measuring circuitry 5 acquires the measured potential difference or the impedance value as information regarding the potential difference. This information is sent to biological information monitoring device 300.

Biological information monitoring device 300 includes electrocardiographic component feature detection circuitry 7, envelope curve processing circuitry 8, and respiratory information output circuitry 9.

Electrocardiographic component feature detection circuitry 7 (hereinafter referred to as "detection circuitry 7") receives information regarding the potential difference acquired by biological signal measuring device 200a, for example, information on the potential difference in the thorax. Based on the information on the potential difference, detection circuitry 7 detects S wave peaks from among electrocardiographic peaks including P wave peaks, Q wave peaks, R wave peaks, S wave peaks, and T wave peaks. Examples of methods for detecting the S wave peaks are as follows.

EXAMPLE 1

Figure 1:
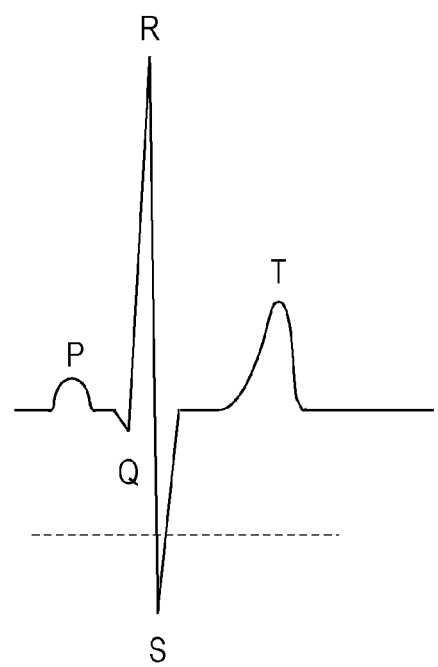
FIG. 1 is a waveform chart illustrating one cycle of basic electrocardiographic components.
Figure 2A:
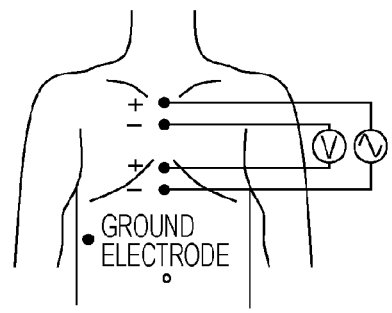
FIG. 2A is a diagram illustrating a concept of a method described in NPL 1.
Figure 2B:
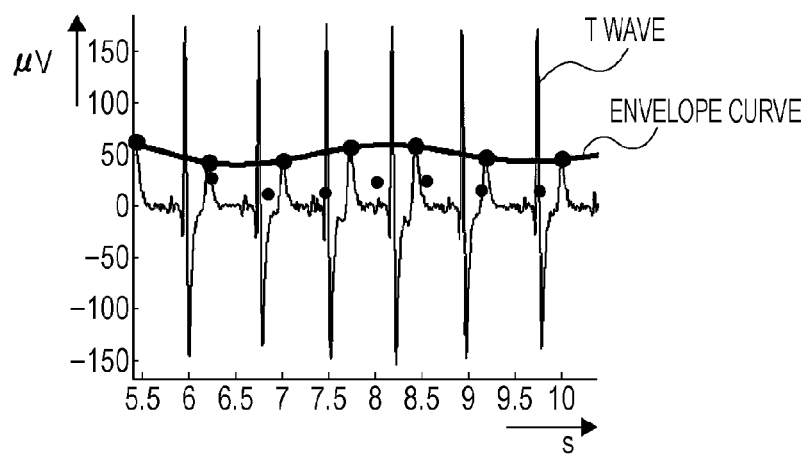
FIG. 2B is a diagram illustrating the concept of the method described in NPL 1.
Figure 2C:
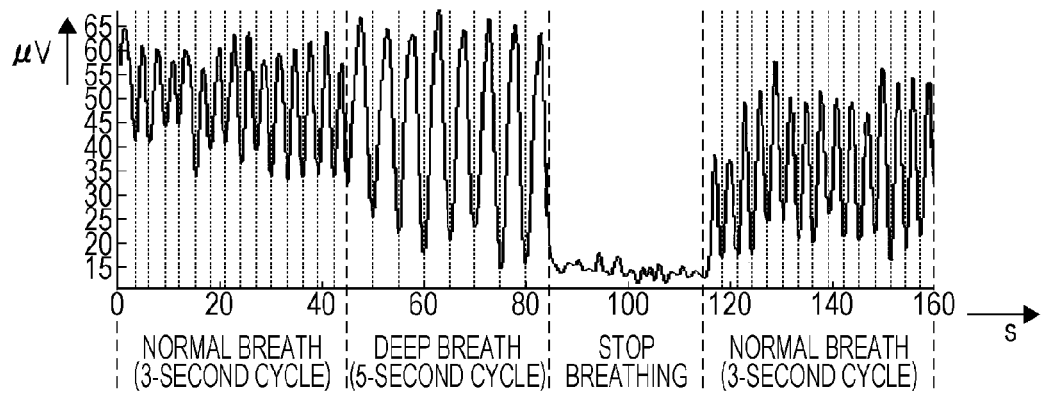
FIG. 2C is a diagram illustrating the concept of the method described in NPL 1.

Based on the information regarding the potential difference acquired by biological signal measuring device 200a, detection circuitry 7 detects, as the S wave peak, a peak that is equal to or less than a predetermined threshold (for example, a value of the dashed line in FIG. 1) in one electrocardiographic cycle. For example, a period between a first R wave peak and a second R wave peak that each have a peak equal to or greater than a predetermined threshold is defined as one electrocardiographic cycle.

EXAMPLE 2

Based on the information regarding the potential difference acquired by biological signal measuring device 200a, detection circuitry 7 detects the R wave in one electrocardiographic cycle, and then detects a minimum value after the R wave as the S wave peak.

EXAMPLE 3

Based on the information regarding the potential difference acquired by biological signal measuring device 200a, detection circuitry 7 detects the R wave and the T wave in one electrocardiographic cycle, and detects, as the S wave peak, a peak having polarity opposite to polarity of the R wave and the T wave, the peak existing between the R wave and the T wave.

An implementation form of detection circuitry 7 as hardware may be a potential sensor, and may be a PC, a smart phone, and a tablet. By executing installed software (a computer program), a CPU of a PC, a smart phone, or a tablet receives information regarding the potential difference transmitted by wire or wireless from potential-measuring circuitry 5, and detects the S wave peak by information processing according to the software.

As another extraction method of respiratory information by processing circuitry 8, for example, in a case where the S wave peaks are obtained periodically, an electrode floats temporarily due to motion of the user, and a specific S wave peak disappears in some cases. In this case, a time corresponding to the specific S wave peak is specified, measured values before and after the time of the S wave are used to calculate a representative value that replaces the S wave peak, and a curve of the respiratory component may be calculated from the representative value. As the representative value, an average of previous S wave peaks may be used, for example.

An implementation form of processing circuitry 8 as hardware may be a potential sensor, and may be a PC, a smart phone, and a tablet. By executing installed software (a computer program), a CPU of a PC, a smart phone, or a tablet may extract the respiratory information (the envelope curve) by information processing according to the software.

Respiratory information output circuitry 9 (hereinafter referred to as "output circuitry 9") outputs the respiratory information generated by processing circuitry 8. A form of output may be, for example, a visual output onto a screen or the like, and may be transmission by wire or wireless. In an example of transmission by wire or wireless, the respiratory information can be stored in data storage device 6. A respiratory rate may be output as the respiratory information. For example, processing circuitry 8 determines the respiratory rate from the envelope curve.

An implementation form of output circuitry 9 as hardware is a display device, a communication circuitry, or a communication interface.

Data storage device 6 is, for example, a recording medium and/or a recording device including a recording medium, and stores the respiratory information transmitted from output circuitry 9. Examples of the recording medium may include a semiconductor recording medium, a magnetic recording medium, and an optical recording medium. Measuring circuitry 5, detection circuitry 7, processing circuitry 8, and output circuitry 9 may be constituted as one CPU. For example, measuring circuitry 5, detection circuitry 7, processing circuitry 8, and output circuitry 9 are also generically denoted as a circuitry.

(Overall Processing Flowchart)

Figure 10:
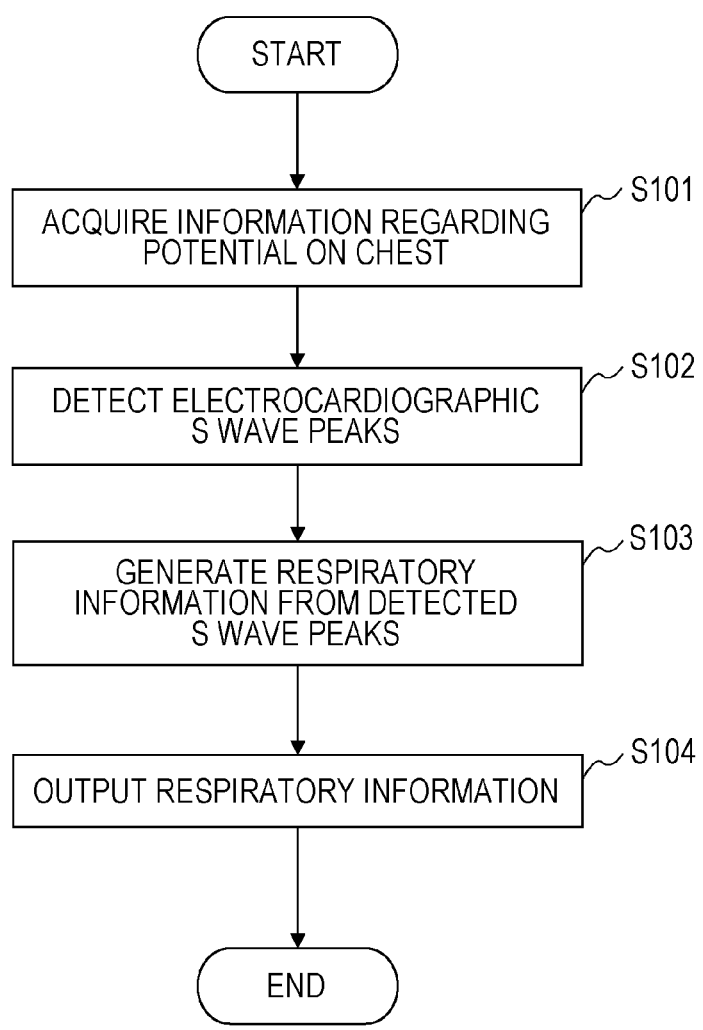
FIG. 10 is a flowchart illustrating an overall processing flow of biological information monitoring system $100a$ according to the exemplary embodiment.

FIG. 10 is an overall processing flowchart of biological information monitoring system 100a according to the present exemplary embodiment.

<Step S101>

Potential-measuring circuitry 5 of biological signal measuring device 200a measures the potential difference from the two electrodes placed on the thorax (right thorax) of the user to acquire information regarding the potential. The information regarding the potential may be a potential difference and may be an impedance value.

<Step S102>

Detection circuitry 7 detects the S wave peak based on the potential difference on the thorax measured in step S101. For example, detection circuitry 7 detects the plurality of S wave peaks.

<Step S103>

Processing circuitry 8 generates the respiratory information from time-series information on the S wave peaks detected in step S102. For example, processing circuitry 8 generates the respiratory information from the time-series information including magnitude of the peak potential included in the plurality of S wave peaks and time of the peaks. More specifically, processing circuitry 8 generates the envelope curve by interpolating between the peaks with a spline curve, and defines the envelope curve as the respiratory information.

<Step S104>

Output circuitry 9 outputs the respiratory information generated in step S103.

By above processing, in a case of acquiring the electrocardiogram of the user through the use of the two electrodes placed in the thorax on the opposite side of the position of the heart, the respiratory information that can be acquired through the use of the S wave peaks is more accurate than the respiratory information acquired through the use of the T wave peaks.

Figure 11:
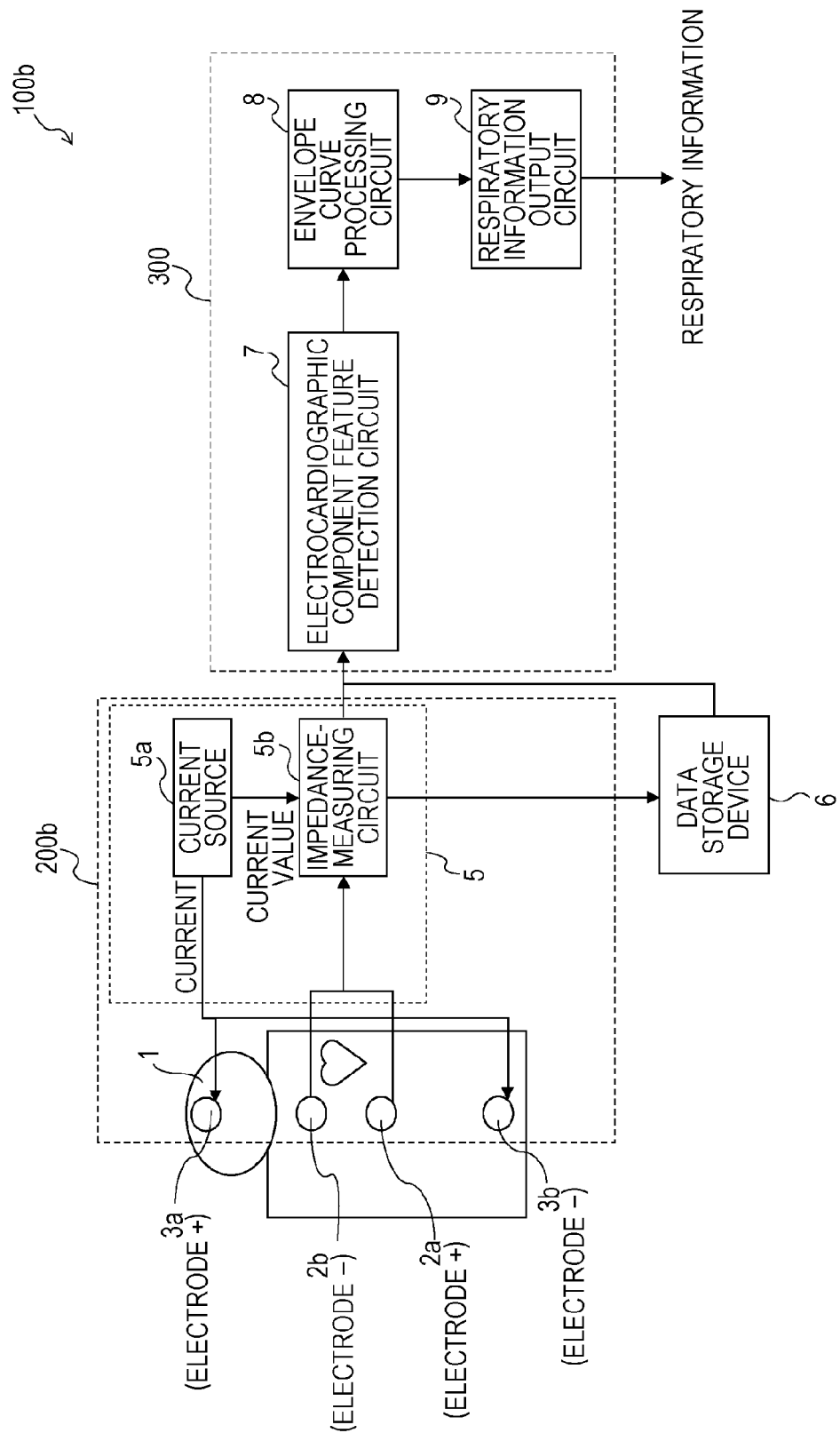
FIG. 11 is a diagram illustrating a configuration of biological information monitoring system $100b$ according to a variation of the exemplary embodiment.

FIG. 11 illustrates a configuration of biological information monitoring system 100b according to a variation of the present exemplary embodiment. Biological information monitoring system 100b measures thoracic impedance by the four-terminal method.

Biological information monitoring system 100b includes data storage device 6, biological signal measuring device 200b, and biological information monitoring device 300.

The configuration of biological information monitoring system 100b differs from the configuration of biological information monitoring system 100a in the configuration of the biological signal measuring device. The following describes only the configuration related to the difference.

Biological signal measuring device 200b measures the potential by using four electrodes 2a, 2b, 3a, and 3b. Electrodes 2a and 2b are potential-measuring electrodes. Electrodes 3a and 3b are current-applying electrodes.

Potential-measuring electrodes 2a and 2b, and current-applying electrodes 3a and 3b are placed in positions that satisfy measurement conditions of the four-terminal method. That is, potential-measuring electrodes 2a and 2b are placed, for example, within a range of passage of an electric current that flows from current-applying electrode 3a to current-applying electrode 3b. More specifically, potential-measuring electrodes 2a and 2b are provided so as to be sandwiched between current-applying electrodes 3a and 3b.

Potential-measuring circuitry 5 includes current source 5a and impedance-measuring circuitry 5b.

Current source 5a supplies an electric current to current-applying electrodes 3a and 3b placed on the thorax of the user. Current source 5a is, for example, a built-in battery (not illustrated) and a circuitry provided for passing a current from the battery. Current source 5a may be configured according to an aspect that does not include the built-in battery.

According to the present exemplary embodiment, current source 5a applies a current having a value (for example, several nano amperes to several hundred microamperes) smaller than a current value (for example, 350 µA) typically used in conventional electrocardiographic measurement. This is because an assumption is made that biological signal measuring device 200b needs to reduce capacity of the battery (not illustrated) due to downsizing or the like. By measuring impedance with a current value lower than the current value that is conventionally applied, it becomes possible to extend drive time of biological signal measuring device 200b. As described above, according to the present exemplary embodiment, current source 5a applies the current having a value smaller than 350 µA.

It is assumed herein that current source 5a applies a sinusoidal alternating current having a current value of ±10 nA.

Impedance-measuring circuitry 5b measures a thoracic impedance value of the user at a plurality of times by using the potential difference between first potential-measuring electrode 2a and second potential-measuring electrode 2b. Specifically, impedance-measuring circuitry 5b measures the potential difference between potential-measuring electrodes 2a and 2b. Impedance-measuring circuitry 5b divides a value of the measured potential difference by the current value applied from current source 5a to acquire a division result as the thoracic impedance value. The thoracic impedance value is sent to detection circuitry 7 as the information regarding the potential difference.

Hereinafter, processing is performed by biological information monitoring device 300 as described above. Operation of biological information monitoring system 100b is also performed as illustrated in FIG. 10.

In the present disclosure, all or part of units and devices, or all or part of functional blocks in block diagrams illustrated in FIG. 9 and FIG. 11 may be executed by one or more electronic circuitries including a semiconductor device, a semiconductor IC (Integrated Circuitry), or an LSI (Large Scale Integration). The LSI or IC may be integrated into one chip, and may be constituted through combination of two or more chips. For example, the functional blocks other than a storage element may be integrated into one chip. The integrated circuitry that is called LSI or IC here is also called differently depending on degree of integration, and may be called a system LSI, VLSI (Very Large Scale Integration), or ULSI (Ultra Large Scale Integration). For an identical purpose, it is possible to use an FPGA (Field Programmable Gate Array) that is programmed after manufacture of the LSI, or a reconfigurable logic device that allows reconfiguration of connection inside the LSI or setup of circuitry blocks inside the LSI.

Furthermore, part or all of functions or operations of units, devices, or part or all of devices can be executed by software processing. In this case, the software is recorded in a non-temporary recording medium, such as one or more ROMs, optical disks, or hard disk drives. When the software is executed by a processor, the software causes the processor and a peripheral device to execute a specific function within the software. The system or device may include one or more non-temporary recording media that records the software, a processor, and a necessary hardware device, for example, an interface.

The biological information monitoring system according to the present disclosure allows the respiratory information to be extracted, even if the user places the electrodes on the thorax on the opposite side of the position of the heart. This allows the user to do respiration monitoring easily at home, and to measure respiratory information even if electrode positions are different. This can be applied to fields such as checking health conditions at home, and grasping exercise loading conditions in sports. In addition, this can also simplify measurement at a hospital.

REFERENCE SINGS LIST 2a, 2b, 3a, 3b electrode
5 potential-measuring circuitry (measuring circuitry)
6 data storage device
7 electrocardiographic component feature detection circuitry (detection circuitry)
8 envelope curve processing circuitry (processing circuitry)
9 respiratory information output circuitry (output circuitry)
100a, 100b biological information monitoring system
200a, 200b biological signal measuring device
300 biological information monitoring device

What is claimed is:

1. A biological information monitoring system for detecting a respiratory disease, comprising:
    measuring circuitry which, in operation, acquires information on a potential difference between two first electrodes that are configured to be placed on a first area of a thorax of a user, wherein the first area is in a symmetric position with respect to a second area of the thorax that is positioned at the same side as a heart of the user;
    detection circuitry which, in operation, detects a plurality of S wave peaks based on the information on the potential difference to generate time-series information on the plurality of S wave peaks; and
    processing circuitry which, in operation:
        determines respiratory information on the user based on the time-series information on the plurality of S wave peaks; and
        outputs, for the detecting of the respiratory disease, the respiratory information as biological information of the user.

2. The biological information monitoring system according to claim 1, wherein the respiratory information includes an envelope of S wave peak values of the plurality of S wave peaks.

3. The biological information monitoring system according to claim 1, further comprising a current source which, in operation, supplies a current to the two first electrodes,
    wherein, when the current source supplies the current to the two first electrodes, the measuring circuitry, in operation:
    measures the potential difference between the two first electrodes; and
    calculates an impedance value as the information on the potential difference, based on i) the current supplied from the current source and ii) the measured potential difference.

4. A biological information monitoring system according to claim 3, wherein the processing circuitry, in operation:
    determines S wave peak values of the plurality of S wave peaks based on chronological data of the impedance value, wherein the S wave peak values include a component of electrocardiographic origin; and
    generates an envelope of the S wave peak values as the respiratory information.

5. The biological information monitoring system according to claim 1, wherein the respiratory disease is sleep apnea.

6. A method for monitoring biological information for detecting a respiratory disease, the method comprising:
    acquiring information on a potential difference between two first electrodes that are configured to be placed on a first area of a thorax of a user, wherein the first area is in a symmetric position with respect to a second area of the thorax that is positioned at the same side as a heart of the user;
    detecting a plurality of S wave peaks based on the information on the potential difference to generate time-series information on the plurality of S wave peaks;
    determining respiratory information on the user based on the time-series information on the plurality of S wave peaks; and
    outputting, for the detecting of the respiratory disease, the respiratory information as biological information of the user.

7. The method for monitoring biological information according to claim 6,
    wherein the respiratory information includes an envelope of S wave peak values of the plurality of S wave peaks.

* * * * *